United States Patent
Moilanen et al.

(10) Patent No.: US 10,751,026 B2
(45) Date of Patent: Aug. 25, 2020

(54) SKELETAL METHOD AND ARRANGEMENT UTILIZING ELECTROMAGNETIC WAVES

(71) Applicant: Oscare Medical Oy, Vantaa (FI)

(72) Inventors: Petro Moilanen, Saynatsalo (FI); Jussi Timonen, Jyvaskyla (FI); Vantte Kilappa, Jyvaskyla (FI); Pasi Karppinen, Helsinki (FI); Edward Haeggstrom, Helsinki (FI); Timo Karppinen, Helsinki (FI); Zuomin Zhao, Oulu (FI); Risto Myllyla, Oulu (FI)

(73) Assignee: OSCARE MEDICAL OY, Vantaa (FI)

( * ) Notice: Subject to any disclaimer, the term of this patent is extended or adjusted under 35 U.S.C. 154(b) by 1307 days.

(21) Appl. No.: 14/266,188

(22) Filed: Apr. 30, 2014

(65) Prior Publication Data
US 2014/0243666 A1    Aug. 28, 2014

Related U.S. Application Data

(63) Continuation of application No. PCT/FI2012/051053, filed on Oct. 31, 2012.

(30) Foreign Application Priority Data

Nov. 1, 2011    (FI) .................................... 20110378

(51) Int. Cl.
*A61B 8/08*    (2006.01)
*A61B 8/00*    (2006.01)
(Continued)

(52) U.S. Cl.
CPC .......... *A61B 8/0875* (2013.01); *A61B 5/0095* (2013.01); *A61B 5/0097* (2013.01);
(Continued)

(58) Field of Classification Search
None
See application file for complete search history.

(56) References Cited

U.S. PATENT DOCUMENTS

| 5,348,002 A * | 9/1994 | Caro | A61B 5/0095 356/39 |
| 6,041,248 A * | 3/2000 | Wang | G01N 21/4795 600/407 |

(Continued)

FOREIGN PATENT DOCUMENTS

| JP | 2005-125081 | 5/2005 |
| JP | 2008-142531 | 6/2008 |

OTHER PUBLICATIONS

Lamb Waves Detection in a Bovine Cortical Tibia using Scanning Laser Vibrometry by Hapsara et al. pub. Medical Imaging 2008: Ultrasonic Imaging and Signal Processing, Proc. of SPIE vol. 6920, 69200N, (2008) 1605-7422/08/$18 doi: 10.1117/12.770277.*
Japanese Office Action English Translation, Japanese Patent Application No. 2014-537677, dated Jun. 28, 2016.
(Continued)

*Primary Examiner* — Katherine L Fernandez
*Assistant Examiner* — Michael S Kellogg
(74) *Attorney, Agent, or Firm* — Buchanan Ingersoll & Rooney PC (57) ABSTRACT

The object of the invention is a skeletal method utilizing electromagnetic waves to be utilized at least in one of skeletal actuation, skeletal detection and skeletal therapy. In the method is performed at least one of first and second method steps, where in the first method step is generated by means of electromagnetic waves at least one mechanical wave in at least one generation location into the skeleton through soft tissue. In the second method step is detected by means of electromagnetic waves skeletal vibrations due to at least one mechanical wave, is recorded the detected at least one mechanical wave in at least one recording location to form mechanical wave information, and distance of said at (Continued)

least one recording location from said at least one generation location is known, and further in the second method step is determined skeletal properties based on at least one recorded signal.

15 Claims, 3 Drawing Sheets

(51) Int. Cl.
*A61B 5/00* (2006.01)
*A61B 18/18* (2006.01)
*A61B 18/00* (2006.01)

(52) U.S. Cl.
CPC .............. *A61B 5/4504* (2013.01); *A61B 8/40* (2013.01); *A61B 8/4209* (2013.01); *A61B 8/48* (2013.01); *A61B 8/0858* (2013.01); *A61B 8/429* (2013.01); *A61B 18/18* (2013.01); *A61B 2018/00339* (2013.01); *A61B 2018/00565* (2013.01)

(56) References Cited

U.S. PATENT DOCUMENTS

| | | | | |
|---|---|---|---|---|
| 6,466,806 | B1* | 10/2002 | Geva | A61B 5/0095 600/310 |
| 2003/0191409 | A1 | 10/2003 | Yost et al. | |
| 2004/0077949 | A1* | 4/2004 | Blofgett | A61B 5/0088 600/472 |
| 2005/0004457 | A1* | 1/2005 | Moilanen | A61B 8/0875 600/437 |
| 2005/0187471 | A1* | 8/2005 | Kanayama | A61B 5/0091 600/437 |
| 2008/0173093 | A1* | 7/2008 | Wang | A61B 5/0073 73/602 |
| 2011/0188251 | A1* | 8/2011 | Kalms | A61B 5/0059 362/259 |

OTHER PUBLICATIONS

Office Action dated Jan. 20, 2020, by the Indian Patent Office in corresponding Indian Patent Application No. 916/KOLNP/2014, and an English Translation of the Office Action. (7 pages).

* cited by examiner

SKELETAL METHOD AND ARRANGEMENT UTILIZING ELECTROMAGNETIC WAVES

CROSS-REFERENCE TO RELATED PATENT APPLICATIONS

The present application is a continuation of International Application No. PCT/FI2012/051053, filed on Oct. 31, 2012, which claims priority to Finnish Patent Application No. 20110378, filed on Nov. 1, 2011, the contents of which are incorporated herein by reference in their entireties.

THE FIELD OF THE INVENTION

The invention relates to skeletal quantitative ultrasound (QUS), included with photo-acoustic (PA) excitation and/or detection of ultrasonic signals in bone.

THE STATE OF THE ART

Essentially, the excitation and/or detection is proposed to be done by means of a beam of electromagnetic wave or impulse waveform, produced e.g. by a laser or pulsed laser source, which is mediated via electromagnetic waveguide (e.g. an optical fibre, collimator, lenses, masks and/or an arrangement of mirrors) and targeted onto the human tissue. An input of the electromagnetic wave into the human tissue is followed by electromagnetic-mechanical conversion (e.g. photo-acoustic conversion) which generates heat and mechanical vibration into the tissue. Correspondingly, at an output of electromagnetic waves, mechanical vibrations of the tissue are detected (e.g. by means of optical interferometry, optical coherence tomography or laser Doppler vibrometry). The objective is thereby to generate and/or detect mechanical waves (e.g. ultrasonic waves) in a bone, bones or the skeleton. The potential applications relate to assessment and therapy of a bone, bones or the skeleton. Bone assessment can include screening or diagnosing of bone disease, such as osteoporosis, and monitoring of fracture healing. Therapy can include, e.g., facilitation of fracture healing by mechanical vibration.

In particular, the invention relates closely to earlier U.S. Pat. No. 7,601,120 B2 (Petro Mollanen et al) on noninvasive assessment of bones, which proposes simultaneous in vivo QUS measurement of two or more modes of Lamb waves in human long bones such as the radius and tibia. Such measurement is based on so-called axial transmission technique, which refers to excitation and detection at a given source receiver distance (or a number of distances) along the long axis of a bone. In particular, one of the said ultrasonic modes can be associated to the first arriving signal (FAS) and the other one to fundamental flexural (i.e. antisymmetric) Lamb mode (A0).

The speed of sound of the FAS can be interpreted according to those of the fundamental symmetric Lamb mode (S0) and lateral compression wave (Nicholson et al 2002; Bossy et al 2002). The lateral compression wave is a compression wave which propagates along the outer (periosteal) boundary of the bone, at a velocity closely consistent with that of a bulk compression wave. In particular, the FAS appears as a transient mode of which apparent propagation velocity can be assessed from the time of flight together with the known source-receiver distance. A number of source-receiver distances and measurement of propagation at two opposite directions with symmetrical arrangement of sources and receivers is needed in order to correct for the delays in the time of flight due to passing through the soft coating tissue. Such correction is possible by traditional ultrasonic means, an array of piezoceramic contact ultrasound transducers, which has shown on in vivo studies to provide good assessment of bone mineral density and cortical thickness in particular when the centre frequency of excitation is tuned sufficiently low (preferably 100-400 kHz) (Kilappa et al 2011). Moreover, this approach has provided excellent prediction of bone fractures, comparable or better than DXA (Moilanen et al, subm). By today, none of the information above can be considered novel.

A number of Lamb modes can also be excited and detected individually in bone. One of the most particular interest is the A0 Lamb mode, of which velocity is strongly associated to thickness of the cortical bone, and thus essentially enables estimation of cortical wall thickness inversely from the measured ultrasound velocity (Moilanen et al UMB 2007). However, it has shown truly challenging with the traditional ultrasound technique based on piezoceramic contact ultrasound transducers to excite and detect this A0 mode through the soft tissue coating (Mollanen et al 2008). This is explained due to the fact that the soft coating tissue provides a propagation path to interferences, which often are relatively strong, while at the same time the A0 mode is known to have weak displacement amplitude apart from bone, within the surrounding soft tissue. Moreover, as the propagation velocities of the interference modes are close to that of the A0 mode, it is truly challenging to extract the A0 from the response signals recorded on top of the soft coating. Therefore, specific attention is required for tuning the excitation and detection to potentially enable the in vivo measurement of the A0 mode. In addition to A0 Lamb mode, a number of other Lamb modes may prove diagnostically useful.

Bone strength (or fragility) is determined by a number of properties, such as elastic stiffness, bone mineral density, porosity and cortical thickness. In particular, it has been shown that microscopic porosity of cortical bone is the major determinant which describes variations between individuals in elastic stiffness or bone mineral density (Granke at al 2011). The porosity on the other hand is known to be one important factor, in addition to cortical thickness, which describes the fragility of cortical bone (Yeni et al 1997, Zebaze et al 2010). The bone fragility is thus determined by multiple factors, which could most completely be assessed by ultrasound. To this end, however, multimodal ultrasound is clearly needed in order to provide complete characterization of bone fragility. Also these prior art examples indicates that multimodal axial transmission combining e.g. the measurement of the FAS (first arriving signal) and A0 modes is clearly needed in order to provide more complete characterization of bone fragility.

SHORT DESCRIPTION OF THE INVENTION

The object of the invention is to accomplish an improved osteoporosis assessment technology which gives essentially accurate measurement results for the needs of osteoporosis analysis. This is achieved by a skeletal method utilizing electromagnetic waves to be utilized at least in one of skeletal actuation, skeletal detection and skeletal therapy. In the method is performed at least one of first and second method steps, where in the first method step is generated by means of electromagnetic waves at least one mechanical wave at at least one generation location into the skeleton through soft tissue, and in the second method step is detected by means of electromagnetic waves skeletal vibrations due to at least one mechanical wave, is recorded the detected at least one mechanical wave at at least one recording location to form mechanical wave information, and distance of said at least one recording location from said at least one generation location is known, and further in the second method step is determined skeletal properties based on at least one recorded signal.

The focus of the invention is also a skeletal arrangement utilizing electromagnetic waves to be utilized at least in one of skeletal actuation, skeletal detection and skeletal therapy. The arrangement comprises at least one first and second means and, where the first means are for generating by means of electromagnetic waves at least one mechanical wave at at least one generation location into the skeleton through soft tissue, and the second means are for detecting by means of electromagnetic waves skeletal vibrations due to at least one mechanical wave, means for recording the detected at least one mechanical wave at at least one recording location to form mechanical wave information, and distance of said at least one recording location from said at least one generation location is known, and means for determining skeletal properties based on at least one recorded signal.

The invention is based on utilization of at least one of first and second method steps, where in the first method step is generated at least one mechanical wave into the skeleton through soft tissue, and in the second method step is detected skeletal vibrations due to at least one mechanical wave, is recorded the detected at least one mechanical wave to form mechanical wave information, and in the second method step is determined skeletal properties based on at least one recorded signal.

The benefit of the invention is that quality of measurement results of bone properties is improved to be utilized for example in osteoporosis analysis. Also measurement sensors with essentially small dimensions can be used, which enables use of low-frequency for example ultrasound with small and controllable form of mechanical interference to improve controlled excitation of elastic wave modes, and enables miniaturization of for example multielement sensors, and gives both ergonomic benefit in the use of the sensors and economical benefit in the production of the sensors. The invention also enables electromagnetic excitation to be used for therapy purposes to generate mechanical vibration in bone.

In one embodiment of the present application, a method of skeletal assessment utilizing electromagnetic waves comprises detecting skeletal vibrations of at least one mechanical wave from bone through soft tissue, recording the detected skeletal vibrations of at least one mechanical wave in at least one recording location to form mechanical wave information, wherein a distance of said at least one recording location from said at least one generation location is known and non-zero, and further wherein the detecting step includes determining skeletal properties based on at least one recorded signal, wherein the method is performed in vivo method steps, and exciting at least one mechanical wave in at least one generation location into the skeleton through soft tissue by utilizing as required values, wherein the values include values of wavelength, pulse length and form of an excitation spot in order to perform proper excitation through soft tissue to generate said at least one mechanical wave into the skeleton.

In another embodiment of the present application, a skeletal arrangement utilizing electromagnetic waves to be utilized at least in one of skeletal actuation, skeletal detection and skeletal therapy, the arrangement comprises in vivo detection means configured to detect skeletal vibrations of at least one mechanical wave from bone through soft tissue, means for recording the detected skeletal vibrations of at least one mechanical wave in at least one recording location to form mechanical wave information, wherein a distance of said at least one recording location from said at least one generation location is known and non-zero, and the arrangement includes means for determining skeletal properties based on at least one recorded signal, wherein the arrangement includes in vivo excitation means for generating by electromagnetic waves at least one mechanical wave in at least one generation location into the skeleton through soft tissue by utilizing as required values at least values of wavelength, pulse length and form of an excitation spot in order to perform proper excitation through soft tissue to generate said at least one mechanical wave into the skeleton.

DETAILED DESCRIPTION OF THE INVENTION

Figure 1:
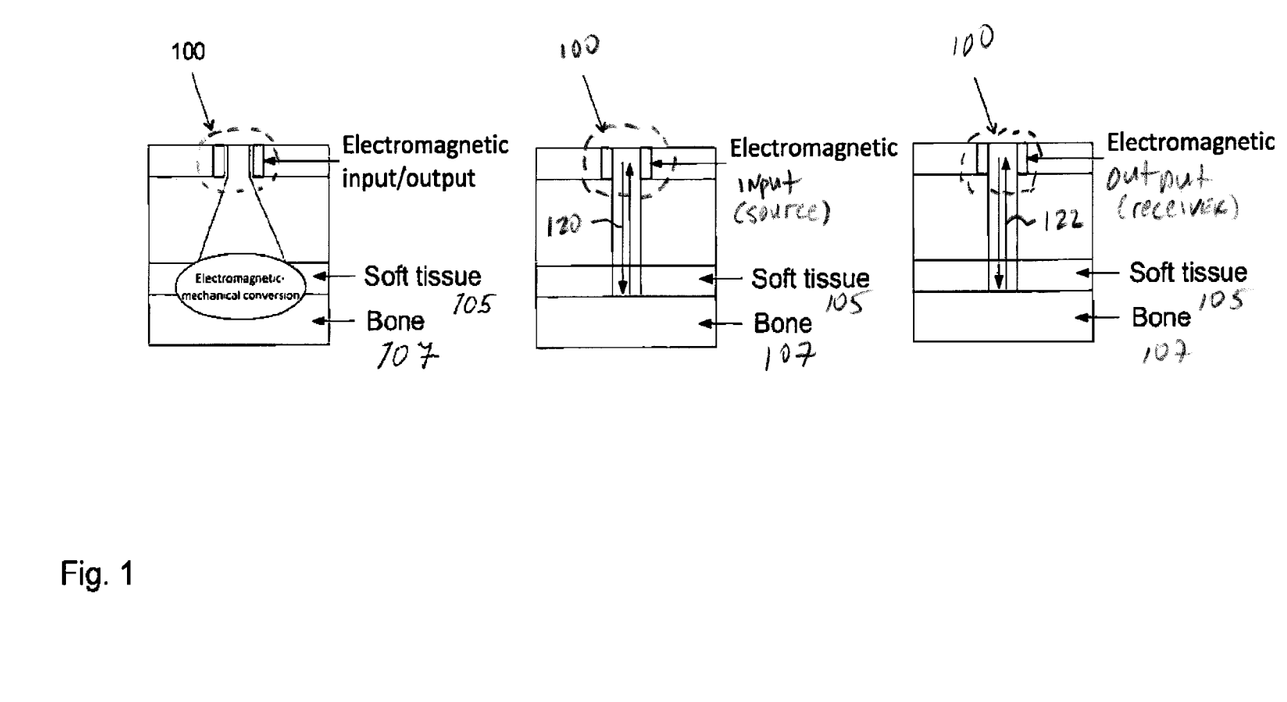
FIG. 1 presents electromagnetic wave excitation and detection according to the present invention.
Figures 2A, 2B:
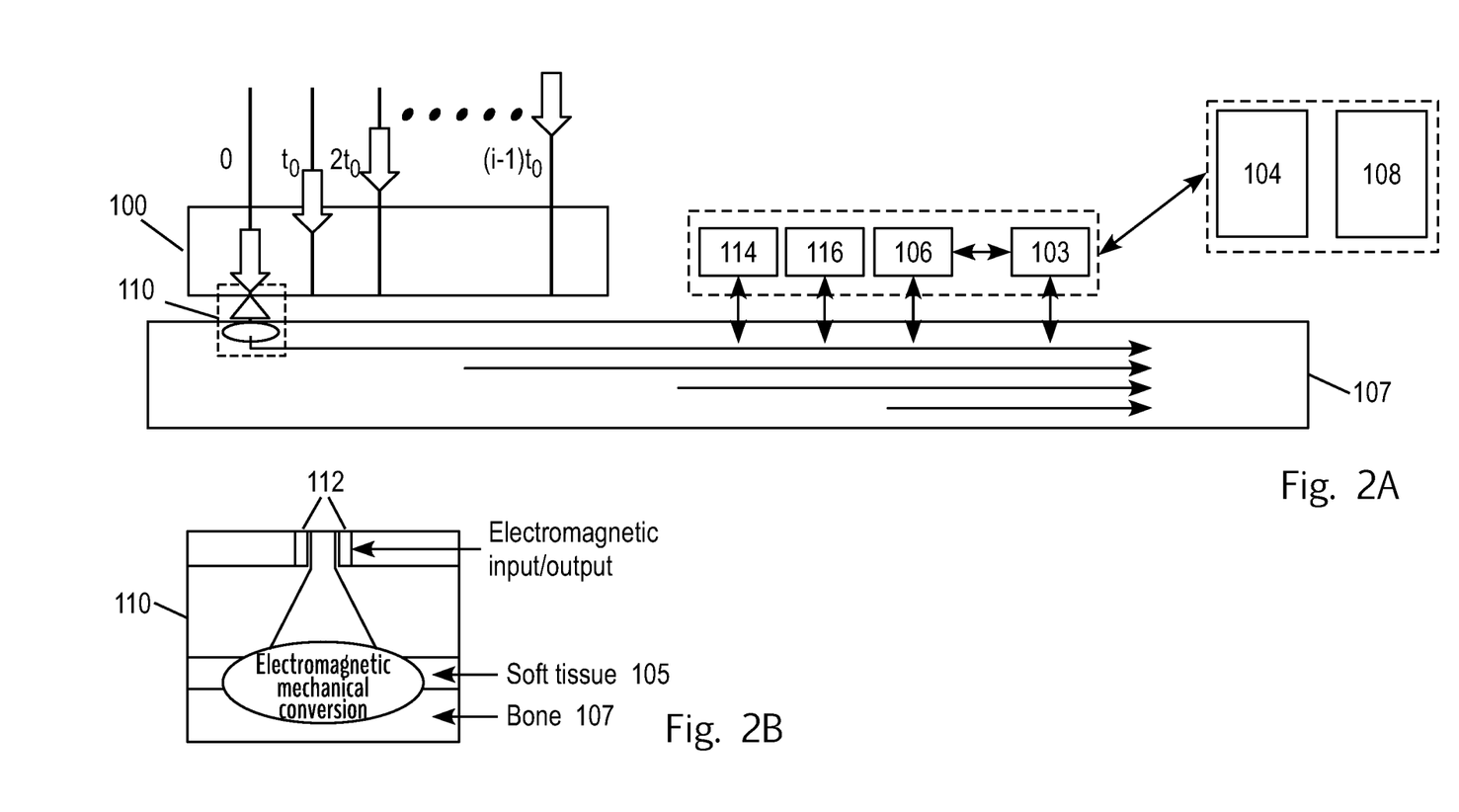
FIG. 2 presents a delayed excitation and detection embodiment according to the present invention.
Figure 3A:
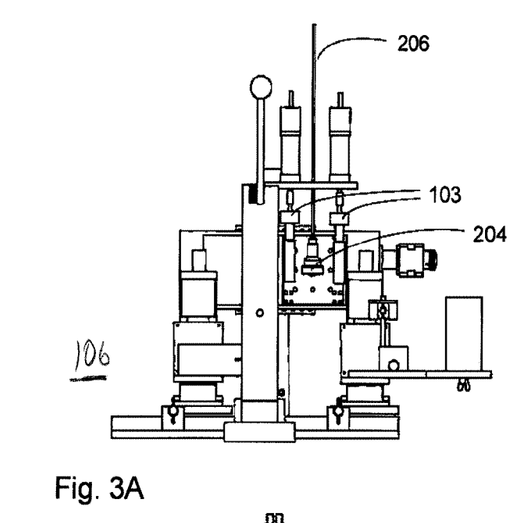
FIGS. 3A-3D present a side (FIG. 3A), front (FIG. 3B), top (FIG. 3C), and an isometric (FIG. 3D) view of an exemplary means for performing positioning movements of electromagnetic wave sensors according to the present invention.
Figure 3B:
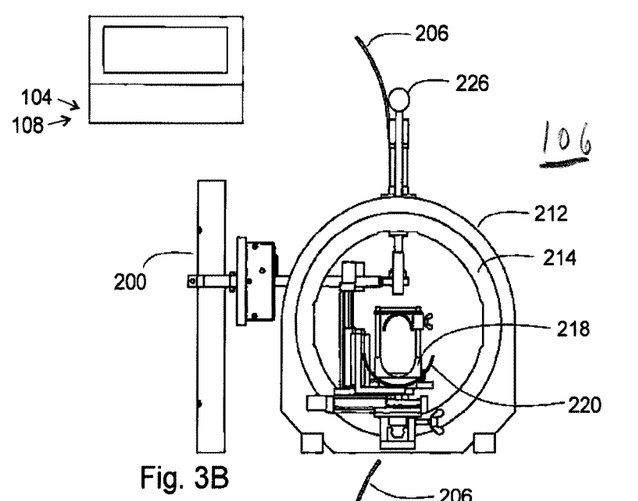
Figure 3C:
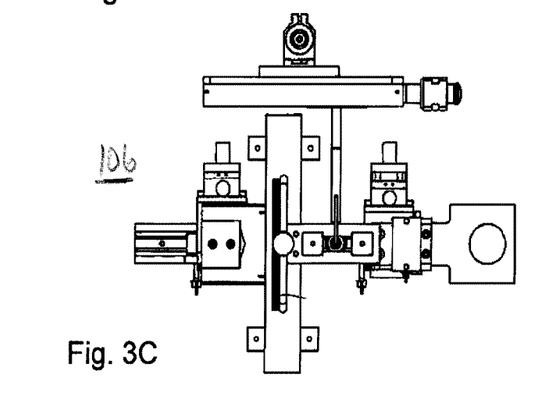
Figure 3D:
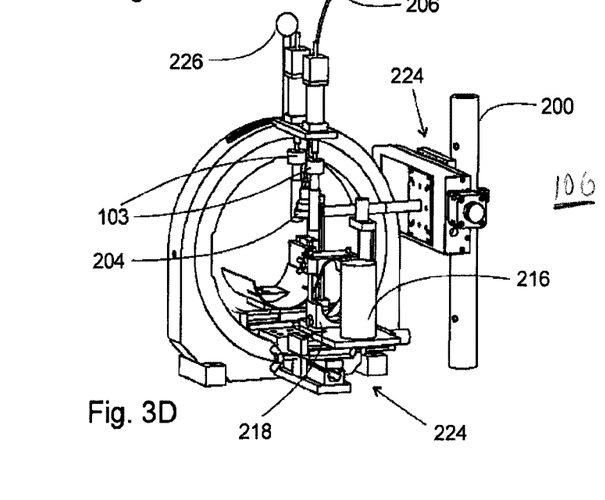

In FIG. 1 is presented electromagnetic wave excitation and detection according to the present invention. Reference number 100 refers to first means 100 for generating by means of electromagnetic waves at least one mechanical wave at at least one generation location into the skeleton 107 through soft tissue 105. Reference sign 120 in FIG. 1 refers to electromagnetic input function performed by the first means 100. Reference sign 122 in FIG. 1 refers to electromagnetic output function. In FIG. 2 is presented as an example a phase delayed excitation and detection embodiment according to the present invention. The arrangement comprises second means 103 for detecting the electromagnetic output. In said detection is detected by means of electromagnetic waves skeletal vibrations due to at least one mechanical wave. In a preferred phase delayed embodiment light beam is guided through an optical fiber where after it is absorbed to the skeleton and generates for example an ultrasound wave. Time-delayed excitation is attained by employing a time delay ($t_o$) between trigger signals of for example laser diodes.

Referring to FIG. 2 the arrangement comprises means 104 for recording the detected at least one mechanical wave at least one recording location to form mechanical wave information. Distance of said at least one recording location from said at least one generation location is known. The arrangement comprises means 108 for determining skeletal properties based on at least one recorded signal. Said means 104, 108 are arranged for example in a computer processor utilizing calculative programs, when needed. The computer processor 104, 108 is presented schematically in the FIG. 2. Wired or wireless data transmission is used between the computer processor 104, 108 and the first 100 and second 103 means to perform data transmissions between them. Said means 103, 104, 108 can be utilized also in other embodiments of the invention than the delayed excitation and detection embodiment of FIG. 2.

In a method according to the invention is performed at least one of first and second method steps, where in the first method step is generated by means of electromagnetic waves at least one mechanical wave at at least one generation location into the skeleton 107 through soft tissue 105. In the second method step is detected by means of electromagnetic waves skeletal vibrations due to at least one mechanical wave, is recorded the detected at least one mechanical wave at at least one recording location to form mechanical wave information, and distance of said at least one recording location from said at least one generation location is known, and further in the second method step is determined skeletal properties based on at least one recorded signal. When whether the first or the second method step is performed, for example means of mechanical and/or piezo-mechanical effects can be utilized together with the first or the second method step and the first 100 or second means 103, 104, 108 utilized in said first or second method step. A therapy embodiment according to the invention can be realized by using the first means 100 according to the first method step.

One preferred arrangement according to the invention comprises means 100 for performing multimodal axial transmission in generation of at least one mechanical wave by means of electromagnetic waves. The arrangement can also comprise means 110 for tuning at least one of center frequency and pattern of the mechanical wave to facilitate an in vivo excitation of at least one Lamb mode into the bone. Means 110 preferably comprise electromagnetic sources, i.e. electromagnetic wave sensors 112, and at least one processor, which in the preferred embodiment of FIG. 2 can be arranged for tuning at least one of center frequency and pattern of the mechanical wave by performing phased delay excitation of an array of the electromagnetic sources 112 to facilitate the in vivo excitation of at least one Lamb mode into the bone. Means 110 can be further arranged for optimizing magnitude of the phase delay by utilizing a feedback based on at least one of maximization of an amplitude of detected signal and minimization of bandwidth of detected signal, and means 108 for determining the phase velocity of the Lamb mode excited on the basis of the magnitude of the phase delay together with an average distance between the sources in the array of electromagnetic sources 112.

The second means 103 for detecting (FIG. 2) by means of electromagnetic waves skeletal vibrations comprise at least one of a optical interferometer, optical coherence tomography device and laser Doppler vibrometer, and correspondingly the detection of skeletal vibrations is based on at least one of optical interferometry, optical coherence tomography and laser Doppler vibrometry. The optical interferometer, optical coherence tomography device and laser Doppler vibrometer can also be named as electromagnetic wave sensors. The preferred detection of skeletal vibrations in a bone by the second means 103 is based on the detection of at least one of first arriving signal (FAS) and Lamb ultrasound modes. One preferred arrangement comprises means 114 for identifying at least one Lamb mode in the mechanical wave information, and for determining speed of the at least one mechanical wave on the basis of the identified at least one Lamb mode to evaluate at least one property of the skeleton. Also one preferred arrangement of the invention can comprise means 116 for mapping bone material properties of the skeleton on the basis of the formed mechanical wave information.

In FIGS. 3A-3D is presented means 106 for performing positioning movements of electromagnetic wave sensors 100, 103 by performing at least one of the following movements: tuning movement of perpendicular positioning of the electromagnetic wave sensors, movement of adaptive axial positioning of the electromagnetic wave sensors, movement of tangential positioning of the electromagnetic wave sensors, movement of azimuthal positioning of the electromagnetic wave sensors and axial scanning movement of the electromagnetic wave sensors. FIGS. 3A-3D are explained in details later on in this description.

In following description is described in details one of the preferred modes of the present invention. Photo-acoustic (=PA, later on in this description) means, i.e. electromagnetic wave sensors, essentially enable flexible tuning of the excitation and detection which, by a number of ways, can facilitate the in vivo excitation and detection of Lamb waves in human bones. The idea is to generate a mode that is strong and easy to recognize at the receiver. This mode should also be sensitive to at least one clinically relevant property of bone (e.g. cortical bone thickness, elastic stiffness or bone mineral density).

Tuning of excitation and/or detection by PA can be comprised of the following aspects: A. Tuning of optical wavelength (wavelength of the electromagnetic beam) so as to provide maximal light absorption in the bone conditioned on minimizing the absorption in the covering soft tissue. The ultrasonic source (i.e. source of mechanical waves) is thereby generated into the bone or as close to the bone as possible. B. Tuning of illuminated surface area so as to provide maximum allowable light intensity on the skin. C. Tuning of the shape of an illuminated surface so as to produce the strongest possible targeted mode at the receiver. Optimal shape can be, e.g., a sphere, line or crest. D. Tuning of the mechanical (e.g. ultrasonic) centre frequency of excitation, so as to provide (a) optimal excitability and (2) sufficient (or optimal) sensitivity to at least one clinically useful property of bone. E. Tuning of the magnitude of phase delay in the case of phase delayed excitation, so as to facilitate selective excitation of one particular mode.

While an array of contact ultrasound transducers already enable accurate assessment of the first arriving signal (FAS) velocity, the following points, related to excitation, could enhance the FAS measurement. Consider an array of contact ultrasound sources and two contact ultrasound receivers, one at each end of the source array.
1. Replacement of contact US sources by PA means (optical fibre or lasers diodes) enables to increase the number of sources due to a smaller element diameter. The accuracy of ultrasound velocity assessment can thus be increased.
2. Position of the photo-acoustic source or an array of photo-acoustic sources can easily be scanned, so as to further increase the accuracy of velocity determination.
3. PA means can enable rapid tuning of the acoustic centre frequency of excitation, so as to enable assessment of dispersion of the FAS velocity, successively from rapidly iterated measurements by scanning the centre frequency. Such dispersion assessment is supposed to provide a way for FAS based cortical thickness estimation, as an alternative to the A0 Lamb mode.

Excitation and detection of the A0 mode can largely be affected by appropriate tuning of the source 100 and receiver 103. The following approaches of tuning the excitation can thus be considered:
1. Excitation of interference modes into the soft tissue coating should be minimized and excitation of a Lamb A0 mode in bone should be maximized.

Ways to minimize the energy excited into the soft tissue coating and maximize that excited into the A0 mode in bone.
2. Proper choice of the optical wavelength to minimize optical absorption in the soft tissue. The lower the optical absorption the weaker the PA source is. When the PA source is weak in the soft tissue, energy excited into interference modes in the soft tissue is also weak.
3. Proper choice of the optical wavelength to minimize optical scattering, so as to enable sharp beam towards the bone.
4. Proper choice of optical wavelength to maximize the optical absorption in bone, so as to produce a strong PA source in the bone.
5. Proper tuning of the acoustic excitation frequency, so as to facilitate the excitation of A0 through the soft tissue coating. The A0 is most efficiently excited at very low ultrasonic frequencies, preferably at 20-120 kHz, however, piezo elements of such frequencies have inappropriately large diameter for the purpose. PA means enable point sources at such frequencies.
6. Proper adjustment of the shape and size of area irradiated by the laser (preferably a narrow line), so as to maximize the amount of PA energy within the safety limits for the human tissue, but to minimize the surface area to facilitate the excitation of the A0 Lamb mode. The excitation power is a function of the beam intensity and the surface area irradiated.
7. Phase delayed excitation by an array of sources can be used to further facilitate the excitation of A0.
8. Blocking of disturbing the direct propagation path through the soft tissue coating has shown by initial modeling and in vitro experiments to reduce the intensities of direct interference modes in the soft coating, so as to largely facilitate the detection of the A0 mode at the detector on top of the soft coating. To this end, the detector can also be a traditional contact ultrasound transducer.

Ways to facilitate the detection of A0 mode
1. Tuning the optimal sensitivity of the detector to low ultrasonic frequencies (<120 kHz). This is most optimally done by PA means, such as a laser interferometer.
2. Implementation of a point or narrow line detector, also enabled by PA means.
3. Using optical clearing techniques of the soft tissue coating to let the detector beam penetrate close to the bone surface. (This technique has shown to be challenging and potentially impossible to implement).

PA (Photo-acoustics) measurements require clamping of the forearm or lower leg and guiding the source(s) and receiver(s) into an appropriate position with respect to the bone to be measured. It is a task to design such an apparatus suitable for clinical measurements.
1. Important features are convenient position adjustments and appropriate feedback based on the ultrasound signal being measured during the fine adjustments of the position. The main requirements are reasonably rapid and reproducible positioning.

Alternatively, the PA source could be packed together with contact US receivers inside a hand-held probe. Such a design could be implemented by a laser diode or an array of laser diodes, combined potentially with miniature translation stage to provide means for scanning of the source position. Such a setup could provide a potential embodiment for the hybrid device.

2. According to the experience from present US devices, a hand-held probe together with instant response from the measured signal enable intuitive positioning.

Alternatively, the PA source could be packed together with one or two PA receivers inside a hand-held probe, wherein the source is implemented by a laser diode or an array of laser diodes and the receiver by, e.g., a pair of interferometric detectors. Such a design could provide a potential embodiment for the full PA device, suitable for clinical use.

The novel and inventive characters of the invention can be considered to arise at least from the following few facts:
1. Combination of known photo-acoustic (PA) methods with known methods of skeletal quantitative ultrasound (QUS), in a way which is not obvious. Careful choice of several parameters (such as optical wavelength, beam intensity and dimensions of illuminated area at the skin, tuning the PA source for optimal acoustic wavelength, and potentially hampering the propagation of interference modes) is required to be done simultaneously.
2. PA means enable flexible tuning of the excitation (and detection).
   A. Point or point-like (including thin line) sources are enabled also at very low ultrasonic centre frequencies (f=20-120 kHz), which are not possible by piezo ceramic elements of which physical diameter is large when tuned to such frequencies. Additionally, PA means also enable implementation of point-like detectors. The point-like source and receivers are known to be optimal for facilitating the excitation and detection of the A0 Lamb mode in particular (useful also for other modes), including that excitability of the A0 mode typically increases with decreasing frequency.
   B. Instantaneous tuning of the centre frequency of ultrasonic excitation by certain PA sources (laser diodes), so as to enable dispersion assessment of transient ultrasound modes (such as the FAS). Such tuning of the centre frequency is not possible by piezo elements (for short transients). Dispersion of the FAS is sensitive to cortical thickness whereas a FAS measurement at a fixed frequency is mostly sensitive to elastic stiffness and bone mineral density.
   C. Phase-delayed excitation to further facilitate the excitation of ultrasonic modes. Advantages of PA arise from the possibility to point-like sensor elements, which enable inclusion of several sensor elements inside a short clinical array probe.
3. Device design which may be of critical importance for the success with clinical applications of the method proposed.

The arrangement development according to the one preferred embodiment will specifically aim at enabling clinically relevant in vivo measurements of the thickness-sensitive SGW mode (=consistent with Lamb A0). To this end the specific objectives of the project are:
   To introduce a PA technique for wide-band (low-frequency) and flexible signal generation in bone.
   To use PA to selectively excite the A0 mode as a means to reduce mode distortion caused by the overlying soft tissue.
   To use PA to remotely image bone surface vibrations from above the overlying soft tissue.
   To optimize the technique for accurate and fast scanning of the measured distance long enough for clinical use.
   To optimize by modelling the measuring setup for in vivo measurements on bone.

To optimize signal processing for enabling clinical in vivo measurements.

To design and construct a portable instrument.

These objectives will enable clinically relevant multi-mode (FAS+SGW) in vivo characterization of osteoporosis, which will be relatively inexpensive and which will provide a more complete assessment of bone than has been possible thus far.

Different options of implementation of the PAQUS (photo-acoustic skeletal quantitative ultrasound) devices will be investigated.

1. Replacement of the source and receiver of the ultrasonic axial transmission scanner (FIG. 1) by non-contact (photo-acoustic; PA) means.

A. Phase 1: Hybrid device—PA source combined with contact ultrasound detection.

B. Phase 2: Full PA implementation—excitation and detection by PA means.

Enhancement of excitation by using a (PA) phased delay array probe. Direct assessment of cortical thickness from the specular reflection (pulse-echo measurement), as implemented by PA means.

The two clinically useful properties of elastic guided waves (Lamb waves) are thickness-sensitivity and sensitivity to material properties. The latter depends on penetration depth and characteristic vibration profile of each specific mode.

The slow guided wave (SGW or Wave2) is consistent with properties of the A0 Lamb mode. The fast first arriving signal (FAS or Wave1) is an apparent mode observable in the measured signal and its velocity can be interpreted. Ranges of optimal thickness-sensitivity of the FAS and SGW can be interpreted according to the appropriate models.

Influence of the soft overlying tissue is particularly challenging for excitation and detection of the SGW (associated to A0) in particular, due to rapid leakage of the acoustic energy into the surrounding tissue (which causes rapid attenuation with distance) and characteristic displacement profile according to which this mode has detectable displacement amplitude in bone but the amplitude drops rapidly in soft coating, apart from the bone, and is thus hardly detectable on top of the coating (Viktorov 1967; Yapura and Kinra, 1995). Moreover, interferences due to other stronger modes in the coating hamper identification of the weak A0 mode (Moilanen et al., 2008).

The choice of long wavelength (low frequency) can, to some extent, reduce this soft tissue impact. For a particularly long wavelength the A0 mode can have a measurable displacement even on top of the (thin) soft coating. To this end, frequencies as low as, e.g, 50 kHz can be considered optimal. Photo-acoustics enables excitation and detection of such low frequencies while the same would be challenging with piezo-elements due to large physical dimensions of such transducers. For excitation of the A0 mode, sharp (i.e. mediated onto a small surface area) and strong impulse, perpendicular to the elastic waveguide, is indeed known to be optimal.

Energy of an optical signal is mediated into the energy of an acoustic signal (i.e. ultrasound) via photo-acoustic transformation. While this process occurs due to optical absorption, efficiency of the photo-acoustic transformation is mainly determined by absorption coefficient, characteristic to each material and optical wavelength. In addition, penetration depth of the optical beam plays a role.

For cortical bone these optical parameters are dependent on wavelength. Cortical bone has highest optical absorption at excitation wavelengths longer than 1400 nm, where the effective penetration depth into cortical bone is about 1 mm. Laser excitation at these wavelengths is thus optimal to generate strongest possible photo-acoustic waves in bone.

Further considerations are needed to mediate the signal through the soft tissue coating. In general, the soft tissue affects optical absorption and scattering, and limits thus efficiently the amount of light energy arriving to bone. For example according to related absorption spectra, absorption is minimal (and thus optimal) at 600-1100 nm (result for the skin). There is thus no direct match between the optimal values for the bone and soft tissue and efficient photo-acoustic excitation is always a tradeoff between absorption in the soft coating and bone. Therefore, care is needed to the choice of optimal excitation wavelength.

In above three exemplary cases, excitation at 532 nm will produce the strongest but smallest PA source which is only located in subsurface of the soft tissue. Features of a traditional contact ultrasound transducer at the soft tissue surface are thus mimicked, with the advantage of tuneable surface area independent of the excitation frequency which is not possible with piezo elements. For a piezo element its dimensions are always functions of the centre frequency. In particular, at low ultrasonic frequencies the physical size of a traditional piezo element limits its suitability for the present application. The wavelength of 532 nm is optimal for the excitation of FAS in particular, while measurement of this wave mode has been designed and optimized for the contact transducers previously (Kilappa et al 2011). Secondly, this wavelength might due to its small surface size also enable excitation of the SGW (associated to A0) through a thin soft coating.

Excitation at 1064 nm wavelength will generate the weakest and biggest PA sources in both soft tissue and bone. Penetration into the bone could enable excitation of the SGW (associated to A0), while the large size of the source is unoptimal for the purpose.

Excitation at 1680 nm wavelength will cause a strong and sharp PA source in the soft tissue and bone, optimal for excitation of the SGW associated to A0. Strong absorption in the soft tissue (stronger than that in bone), on the other hand, may cause adverse interferences between the PA sources in the soft tissue and bone.

Excitation at 1250 nm can be considered the most optimal wavelength for producing a strong SGW associated to A0. At this wavelength there is an absorption peak in bone and the absorption in soft tissue has decreased to the level comparable with that of bone. A preliminary experimental result supports the assumption that at a low ultrasonic frequency range the amplitude spectra excited at 1250 nm wavelength is stronger than that excited at 1680 nm.

The optical beam can be either focussed onto the skin surface or the area of optical exposure can be adjusted by masking an unfocussed beam. Direct focussing of the beam generates a sharp and strong point (or line) source, which is optimal for excitation of the SGW (associated to A0) in particular. Intensity of such focussed beam, however, is hard to control accurately and locally the intensity may easily exceed the limits of safety. Masking of unfocussed beam is thus focussed a more controlled and safe option, even though masking cannot generate such optimal point source than focussing. Sources generated by masking were line sources with the short dimension (width) along the propagation direction. Values of 1-5 mm were considered for the width and 5-15 mm for the length of the line source. Advantage of a larger beam area is mediation of greater amount of energy safely into the tissue, resulting in a stronger response.

In hybrid version of the photo-acoustic axial transmission scanner, the source is implemented by non-contact means whereas the receivers are traditional contact ultrasound transducers. A pair of receivers is used in order to enable bidirectional measurement for the accurate correction of soft tissue effects.

When exciting and detecting ultrasonic signals in bone in vivo by using the PAQUS hybrid setup, for example the FAS mode can be clearly identified in the recorded signals.

Excitation of Individual Lamb modes (e.g. A0 or S0 mode) can be facilitated by phased delay excitation. It has been thus employed a potentially noncontacting IDT (interdigital transducer)-like excitation to allow efficient generation of a Lamb mode (e.g. the S0 or S0 mode). The idea is to generate a mode that is strong and easy to recognize at the receiver. It should also be sensitive to at least one clinically relevant property of bone (e.g. cortical bone thickness, elastic stiffness or bone mineral density). To do so we illuminate four spots (e.g. spheres, lines or crests) on the skin that lie on the shortest line of sight between the transmission and reception area. The size of these spots is chosen to provide maximum allowable light intensity on the skin. Their shape is chosen to so as to produce the strongest possible targeted mode at the receiver. The inter-spot distance is chosen to match the time of flight requirement (spatial phase matching) for a targeted wave mode (e.g. A0 along the radius bone at 50 kHz). The centre frequency of the targeted mode is selected such that it maximizes the amplitude, by minimizing using feedback the absolute bandwidth, of the received signal. The optical spectrum of the Illuminating laser is chosen such that it provides an optimal light absorption profile in the bone conditioned on minimizing the absorption in the covering soft tissue. The temporal profile of each illuminating pulse and the pulsing pattern onto each illuminated spot is chosen such as to produce a sonic pattern that generates a strong mode into the bone. The illumination of the laser spots (temporally and spatially) should fulfil the phase matching requirement like in an IDT transducer (which depends on sound speed in the bone and on the distance between the spots).

PA wave will be coupled into human limb by ultrasonic coupling liquid, reflecting at different tissue boundaries. The echoes propagate back into the PA sensor and are received by a piezo-detector. As cortical bone has much higher acoustic impedance than other soft tissues, the echoes at bone—soft tissue boundaries are much stronger than those reflected from soft tissue-soft tissue boundaries, which are easy to be distinguished. Measuring the time difference of two echoes from bone-soft tissue boundaries, the bone thickness can be estimated if the acoustic speed in the bone is known.

Finally FIGS. 3A-3D are explained more in detail. Proper positioning of an ultrasonic probe into the bone is critical for a successful ultrasound measurement. In particular, the transverse and circumferential directions with respect to the long axis of bone are important. With a hand-held array probe the proper positioning can be found intuitively by manual movements of the probe, using the properties of a measured response signal as a feedback. The proper anatomical position is typically found within the range of 30 degrees.

In a PAQUS setup, when an external laser unit (or units) 210, i.e. source of electromagnetic radiation 210 is used through an optical fibre 216, the degrees of freedom of moving the laser beam(s) are preferably minimized. Especially, it is challenging to arrange rotation of the laser beam. Therefore, it is preferred, that the degrees of freedom required for proper positioning are arranged by moving the human limb into a proper position, while the ultrasonic source(s) and detector(s) 103 remain fixed.

To arrange the rotation of a human limb, a possible embodiment includes two circles 212, 214 of which the outer one 212 is fixed and the inner one 214 has a freedom to rotate. Ultrasonic transducers (PA and conventional ones) are fixed into (or with respect of) the outer circle. In the hybrid setup the transducers include a PA source mediated, e.g., from an external pulse laser unit, and two conventional contact US receivers. Force sensors are included with the US receivers to monitor the contact pressure. The receivers remain fixed, while means are arranged to scan the axial position of the PA source.

The purpose is to position the mass centre of the cross-section of a bone (e.g. radius) into the centre point of the circle, and then rotate the bone into an appropriate angle. The arm is fixed by specific clamps 218 which have been mounted via linear units into the inner circle 214. Reference sign 200 refers to support part 200 to a base structure, and reference sign 226 refers to a crank 226 to move the inner circle 214 in relation to the outer circle. Reference sign 204 refers to an electromagnetic waves collimator 204.

In the following, the human forearm is used as an example of the human limb, and radius as an example of a bone to be measured.

Means 224 to Move the Ultrasonic Sensors

1. Means can be provided to move the ultrasonic sensors 103 away while clamping the forearm, and to return the sensors back to the measurement position.
2. Means can be provided to fine tune the perpendicular position (x) of the ultrasonic sensors 103.

Adaptive Axial Positioning (z-Direction)

1. The forearm is fixed into the elbow and wrist clamps.
2. Means are provided to measure the positions of these two clamps.
3. The distance of the two clamps represents the bone length and is determined from the measured positions.
4. The axial measurement position is determined in a relation to the bone length.
5. Means 124 are provided to move (by a motor) or to guide the movement (by signs indicating "forward", "backward" and "hold") of the forearm into the correct axial position.
6. Axial positions of the two clamps are fixed.

Tangential (x and y) and Azimuthal Positioning

7. The inner circle is rotated to adjust the azimuthal angle.
8. The tangential positions of the two clamps will be adjusted by four independent linear units.
9. Positioning is tuned successively by position measurements and using the measured signals as a feedback. Positioning can be manual or automated.

Axial Scanning

10. Means 224 are provided to successively move the source beam within a limited range (e.g. 30 mm) between the two receivers, the said range being symmetric with respect the two sensors 103.
11. Response signals are recorded at the sensors 103 at each position of the source.

Alternative Configurations

12. In the hybrid setup, the source 210 can be replaced by a laser diode or an array of laser diodes. In this case, an alternative configuration is possible included that the forearm clamp 218 system is fixed into the table and the sources and receivers into the inner rotating ring. Second alternative design includes a hand held array probe in which case the forearm clamp and positioning mechanism is not necessary.
13. The receivers, ie. sensors 103 can be replaced by PA receivers (e.g. interferometers) and the source by conventional ultrasonic transducer or an array of conventional ultrasound transducers.
14. The receivers can be replaced by PA receivers (e.g. interferometers), so as to enable a full PA device.
15. The sources and receivers can also act in an imaging mode, or specific imaging sensors can be included, so as to enable (geometrical) imaging of the limb based on ultrasonic or PA pulse-echo method Imaging can provide additional diagnostic information, such as the profile or map of cortical thickness. Moreover, imaging can be used to determine the orientation of the bone and position of the mass centre of the cross section of the bone, according to which one can automate the positioning of the bone in the mechanism described.

The computer processor 104, 108 is presented schematically in the FIGS. A-3D. Wired or wireless data transmission is used between the computer processor 104, 108 and the positioning means 106 described in FIGS. 3A-3D to perform data transmissions needed between them.

Although the invention has been presented in reference to the attached figures and specification, the invention is by no means limited to those, as the invention is subject to variations within the scope allowed for by the claims.

The invention claimed is:

1. A method of skeletal assessment of a bone beneath a soft tissue utilizing electromagnetic waves, comprising:
tuning an electromagnetic (EM) source for excitation of one or more Lamb modes in the bone to be analyzed by one or more of:
selecting an optical wavelength of an EM beam to be emitted from the EM source, wherein the EM beam is comprised of EM energy that reduces optical absorption of the EM energy in the soft tissue and increases the optical absorption of the EM energy in the bone to be analyzed;
adjusting a shape and size of a surface area of the soft tissue illuminated by the EM beam by selecting a shape of the EM beam for a specified excitation power; and
selecting a mechanical center frequency of excitation for the EM source for excitation of the one or more Lamb modes through the soft tissue;
transmitting, via the EM source at a location relative to the bone, the EM energy through the soft tissue into the bone;
detecting vibrations in the bone to be analyzed by:
detecting, via using one or more sensors, a first arriving signal and at least one of the one or more Lamb modes excited by a mechanical wave generated in the bone;
identifying, in a processor, one or more of the at least one detected Lamb modes; and
determining, in the processor, a speed of the mechanical wave based on the identified one or more Lamb modes to identify at least one property of the bone.
2. The method according to claim 1, wherein the transmission of the mechanical wave is a multimodal axial transmission.
3. The method according to claim 1, wherein detecting the vibrations in the bone includes performing at least one of optical interferometry, optical coherence tomography and laser Doppler vibrometry.
4. The method according to claim 1, comprising:
adjusting, via positioning means,
an azimuthal position, of the one or more sensors relative to the bone to be analyzed.
5. The method according to claim 1, wherein the EM source is a photo-acoustic wave source, and wherein the one or more sensors comprises a contact-based ultrasonic sensor.
6. The method according to claim 1, wherein the EM source includes an array of EM sources and tuning the EM source for excitation of the one or more Lamb modes includes tuning a magnitude of a phase delay between emissions of the electromagnetic beam from each individual EM source of the array.
7. The method according to claim 6, comprising:
tuning the EM source based on feedback of at least one of an amplitude and a bandwidth of the detected first arriving signal to adjust the magnitude of the phase delay.
8. A device comprising:
an electromagnetic (EM) source configured to: generate an EM beam having a shape for realizing a specified excitation power for a soft tissue, the EM source having a mechanical center frequency of excitation for the EM beam to excite one or more Lamb modes in a bone to be analyzed, wherein the EM beam is comprised of EM energy having an optical wavelength for reducing optical absorption in the soft tissue surrounding the bone to be analyzed and increasing optical absorption in the bone to be analyzed;
a sensor configured to detect a first arriving signal and at least one of the one or more Lamb modes resulting from at least one mechanical wave generated in the bone by the EM beam;
a processor configured to detect vibrations in the bone based on the first arriving signal and the at least one of the one or more Lamb modes detected by the sensor, wherein the processor is configured to identify at least one property of the bone based on an identification of one or more of the at least one detected Lamb modes detected by the sensor and a determined speed of the at least one mechanical wave based on the identified one or more Lamb modes.
9. The device according to claim 8, wherein the EM source is configured to generate the at least one mechanical wave as a multimodal axial transmission.
10. The device according to claim 8, wherein the sensor includes at least one of an optical interferometer, an optical coherence tomography device, and a laser Doppler vibrometer.
11. The device according to claim 8, wherein the EM source includes an array of individual EM sources, the EM source being configured to adjust a magnitude of a phase delay between the individual EM sources tuned based on feedback of at least one of an amplitude and a bandwidth of the detected first arriving signal.
12. The device according to claim 11, wherein the individual electromagnetic sources are configured to perform a phased delay excitation having a specified pattern to facilitate generation of the one or more Lamb modes into the bone to be analyzed.
13. The device according to claim 8, comprising:
a positioning means for adjusting
an azimuthal position, of the sensor relative to the bone.
14. The device according to claim 13, wherein the processor is configured to generate an image from data received from the sensor to map bone material properties of the bone to be analyzed.

15. The device according to claim 8, wherein the EM source is a photo-acoustic wave source, and wherein the sensor is a contact-based ultrasonic sensor.

\* \* \* \* \*